Figure 1:
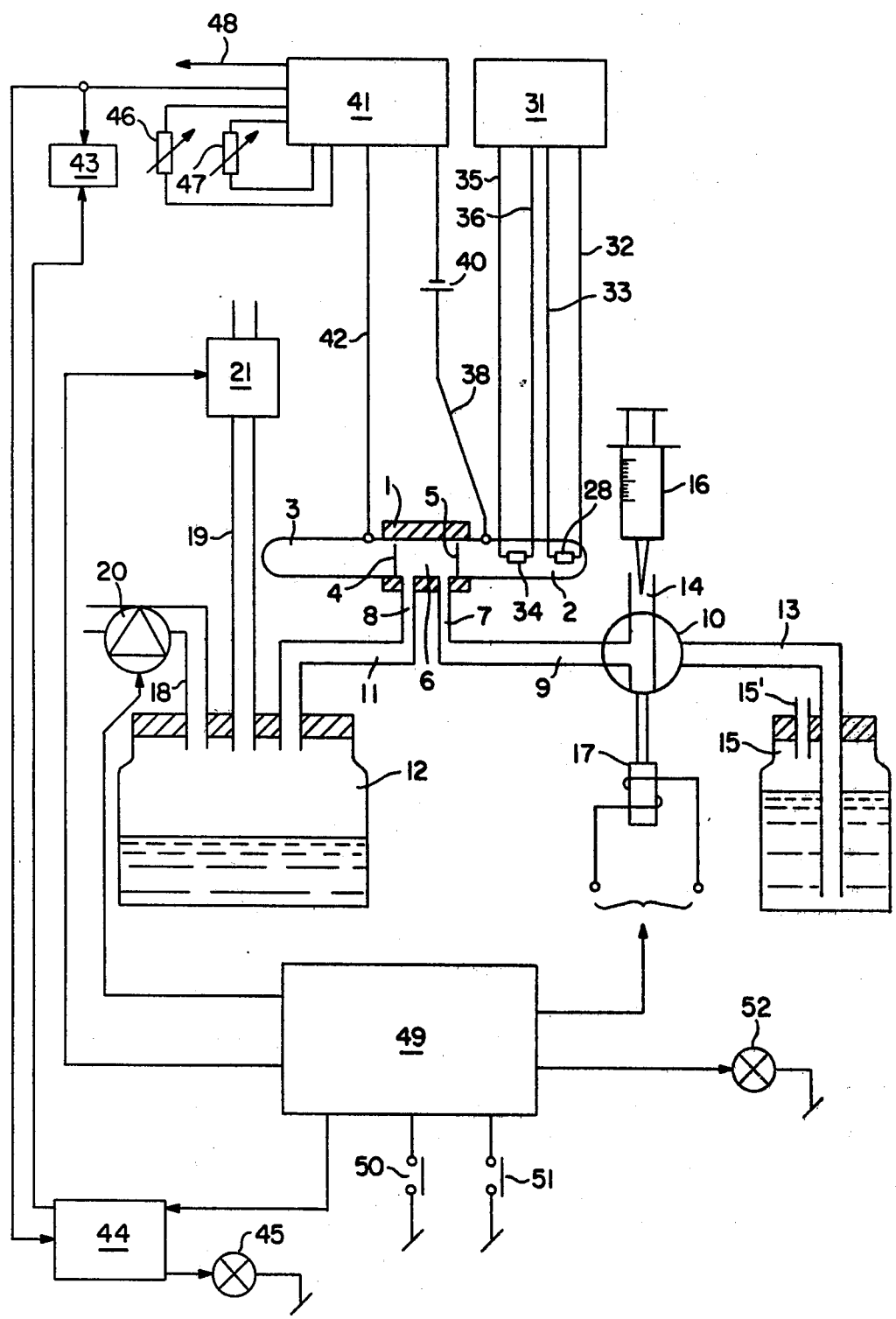

United States Patent [19]

Racine et al.

[11] 4,129,478
[45] Dec. 12, 1978

[54] METHOD FOR MEASURING SUBSTRATE CONCENTRATIONS

[75] Inventors: Philippe Racine, Münchenstein, Switzerland; Jean-Claude Higelin, Hegenheim; Roland Engelhardt, Mulhouse, both of France; Wolfgang Mindt, Erlangen, Germany

[73] Assignee: Hoffmann-La Roche Inc., Nutley, N.J.

[21] Appl. No.: 733,570

[22] Filed: Oct. 18, 1976

Related U.S. Application Data

[62] Division of Ser. No. 493,583, Aug. 1, 1974, Pat. No. 4,005,002.

[51] Int. Cl.² .................................................. G01N 27/46
[52] U.S. Cl. ................................. 204/1 T; 204/195 B; 204/195 P; 195/103.5 R; 195/103.5C
[58] Field of Search ............... 204/1 E, 195 B, 195 P; 195/103.5 R, 103.5 C

[56] References Cited

U.S. PATENT DOCUMENTS

| | | | |
|---|---|---|---|
| 3,526,578 | 9/1970 | Silverman | 204/1 E |
| 3,539,455 | 11/1970 | Clark | 204/1 E |
| 3,623,960 | 11/1971 | Williams | 204/195 P |
| 3,707,455 | 12/1972 | Derr et al. | 204/1 E |
| 3,795,239 | 3/1974 | Eberhard et al. | 204/195 B |
| 3,838,034 | 9/1974 | Groves | 204/195 B |

OTHER PUBLICATIONS

"Analytical Chemistry", 1970, vol. 42. No. 1, pp. 118–121.

*Primary Examiner*—T. Tung
*Attorney, Agent, or Firm*—Jon S. Saxe; George M. Gould

[57] ABSTRACT

The concentration of substrates of enzyme reactions is measured by determining the current produced at an platinum or gold electrode by oxidizing an acceptor utilizing a measuring device comprising a measuring cell, an enzyme electrode in contact with the fluid sample and containing an platinum or gold electrode, an enzyme layer and a reference electrode in contact with the fluid sample. In this manner important physiological parameters, such as the concentration of lactate and glucose in fluid biological samples, can be measured quickly and accurately.

4 Claims, 5 Drawing Figures

METHOD FOR MEASURING SUBSTRATE CONCENTRATIONS

This is a division, of application Ser. No. 493,583 filed Aug. 1, 1974 now U.S. Pat. No. 4,005,002.

The invention relates to a method of measuring the concentration of substrates of enzyme reactions occurring intermediate metabolism, more particularly the concentration of lactate and glucose in fluid biological samples, wherein a current produced at an platinum or gold electrode by oxidising an acceptor is measured by a measuring device substantially comprising a measuring cell for receiving the fluid sample, an enzyme electrode in contact with the test solution and containing an platinum or gold electrode, an enzyme layer and a semi-permeable membrane covering the enzyme layer, and a reference electrode in contact with the fluid sample. The invention also relates to a device for performing the method.

Measurements of the concentration of substrates of the aforementioned kind have become important owing to the results of medical research. It has been shown, for example, that an increase in the lactate concentration in the blood corresponds to a deficiency of oxygen in the cellular region. This knowledge is extremely important, e.g. in treating patients in a condition of shock, since it has been found that in such cases the blood lactate concentration is a critical parameter for judging and following the state of a patient.

In many applications where rapid diagnosis is very important, a method or device for measuring the concentration of substrates in fluid biological samples is of use only if reliable measurements can be rapidly made. More particularly, analytical laboratories and/or hospitals require a measuring device which can suitably automate the measuring processes, which is easy to handle and maintain and for which very small samples are sufficient.

Among methods of the aforementioned kind, the method and the device for performing the method described in the periodical "Analytical Chemistry", 1970, Volume 42, No. 1, pages 118 to 121 has been shown to be particularly advantageous.

The last-mentioned device comprises the enzyme electrode and a second electrode, which, as far as possible, has the same structure as the enzyme electrode.

In each measurement, a substance called the acceptor is added to the fluid sample. The measurement is made by immersing the enzyme electrode, the second electrode and a cathode in the prepared fluid sample, applying a low d.c. voltage between the cathode and the other two electrodes, and measuring the difference between the currents flowing through the enzyme electrode and the second electrode. The second electrode is designed to compensate inaccuracies in the measurement caused by the basic current flowing through the enzyme electrode. The basic current is produced e.g. during the measurement of the blood glucose concentration, since the quinone used as the acceptor is reduced not only by the oxidation of the reduced enzyme but also by the oxidation of various plasma components.

The current used for the measurement flows through the enzyme electrode and is produced as follows: The substrate (S) and the acceptor (Aox) diffuse through the semi-permeable membrane of the enzyme electrode and flow into the enzyme layer thereof. The substrate undergoes an enzymatic reaction. The reduced enzyme (Ered) produced by the reaction is then oxidised in the presence of the acceptor (Aox). The consequently reduced acceptor (Ared) becomes re-oxidised at the platinum or gold electrode of the enzyme electrode. A process coupled in the aforementioned manner can be described by the following overall reaction equations:

$$E + S \rightleftarrows ES \rightarrow Ered + P$$

$$Ered + Aox \rightarrow E + Ared$$

$$Ared \rightarrow A + ne^-$$

P represents a reaction product. The oxidations of the reduced acceptor results in a current which flows through the electrochemical sensor of the enzyme electrode and is specifically related to the concentration of the substrate in the fluid sample.

In the known methods, the following enzymes and acceptors are used, depending on the substrates:

| Substrate | Enzyme | Acceptor |
|---|---|---|
| Glucose | Glucose-Oxidase | Quinone |
| Lactate | Cytochrome b$_2$ | Potassium hexacyanoferrate (III) |

It is also known to regulate the temperature of the container containing the test solution (U.S. Pat. No. 3,623,960) during the measurement. This has an important effect on the accuracy of the measurements, since enzymatic reactions are dependent on temperature.

Like all other known methods, the aforementioned method has the dis-advantage of requiring too much labour and time.

Like all other previously-known devices, the aforementioned device has the following defects: Firstly, the device takes a long time to prepare, since the measurements are not automated and it takes a long time even to regulate the temperature of the test solution. Secondly, the aforementioned devices cannot be operated and maintained by assistant personnel. Thirdly, an excessive quantity of fluid sample is required. Since the minimum dimensions of the container for the test solution depend on the device for regulating the temperature of the fluid sample, the amount of test solution per measurement cannot be reduced. Fourthly, the known device is unsuited for automatic measurements. Fifthly, the basic current cannot be sufficiently accurately compensated by a second electrode, since it is difficult to construct two identical electrodes. Consequently, the aforementioned method and device are unsuitable for performing routine measurements in an analytical laboratory or a hospital.

One object of the invention is to provide a method for determining the concentration of substrates in fluid biological samples, wherein the amount of work and time required is significantly reduced.

Another object of the invention is to provide a device for performing the method according to the invention, which enables measurements to be made rapidly, is simple to operate and maintain, is suitable for automatic measurements and requires only a very small quantity of fluid sample per measurement.

Another object of the invention is to provide an enzyme electrode which can be used in a device for performing the method according to the invention and which can rapidly and very efficiently regulate the temperature of the enzyme-containing layer and enable rapid measurements to be made on very small quantities of test solution.

The method according to the invention is characterised by regulating the temperature of the enzyme-containing layer at a predetermined value, applying a d.c. voltage of approx. 0.25 to 0.50 V between the enzyme electrode and the reference electrode, the enzyme electrode having positive polarity, filling the measuring cell with a buffer solution containing an acceptor, so that a sufficient quantity of the acceptor flows through the semi-permeable membrane of the enzyme electrode into the enzyme-containing layer, sucking the buffer solution from the measuring cell, filling the measuring cell with a fluid sample and measuring the concentration of the enzymereaction substrate contained in the test solution by determining the peak value of the current flowing through the platinum or gold electrode with an electronic circuit.

The invention also relates to a device for performing the method according to the invention, characterised by a measuring-cell system comprising a temperature-controlled enzyme electrode, a reference electrode, a measuring cell in the form of a tubular chamber for receiving the fluid sample, said measuring cell being disposed between the contact surfaces of the electrodes, a temperature-regulating unit coupled to the enzyme electrode in order to regulate the temperature of the enzyme-containing layer a hydraulic device for alternately filling the measuring cell with an acceptor-containing buffer solution or a fluid sample, and an electric indicating device which, after the measuring cell has been filled with a fluid sample, determines the peak value of the current flowing through the platinum or gold electrode, which peak value is representative of the concentration of substrate to be measured.

The invention also relates to an enzyme electrode, more particularly for a device for performing the method according to the invention, characterised in that it comprises a thermometer probe thermally connected to the platinum or gold electrode and provides the temperature-regulating unit with a signal representing the actual temperature of the platinum or gold electrode and is controlled by the temperature-regulating unit so as to regulate the temperature of the platinum or gold electrode and of the enzyme-containing layer in contact with the platinum or gold electrode.

Figure 2:
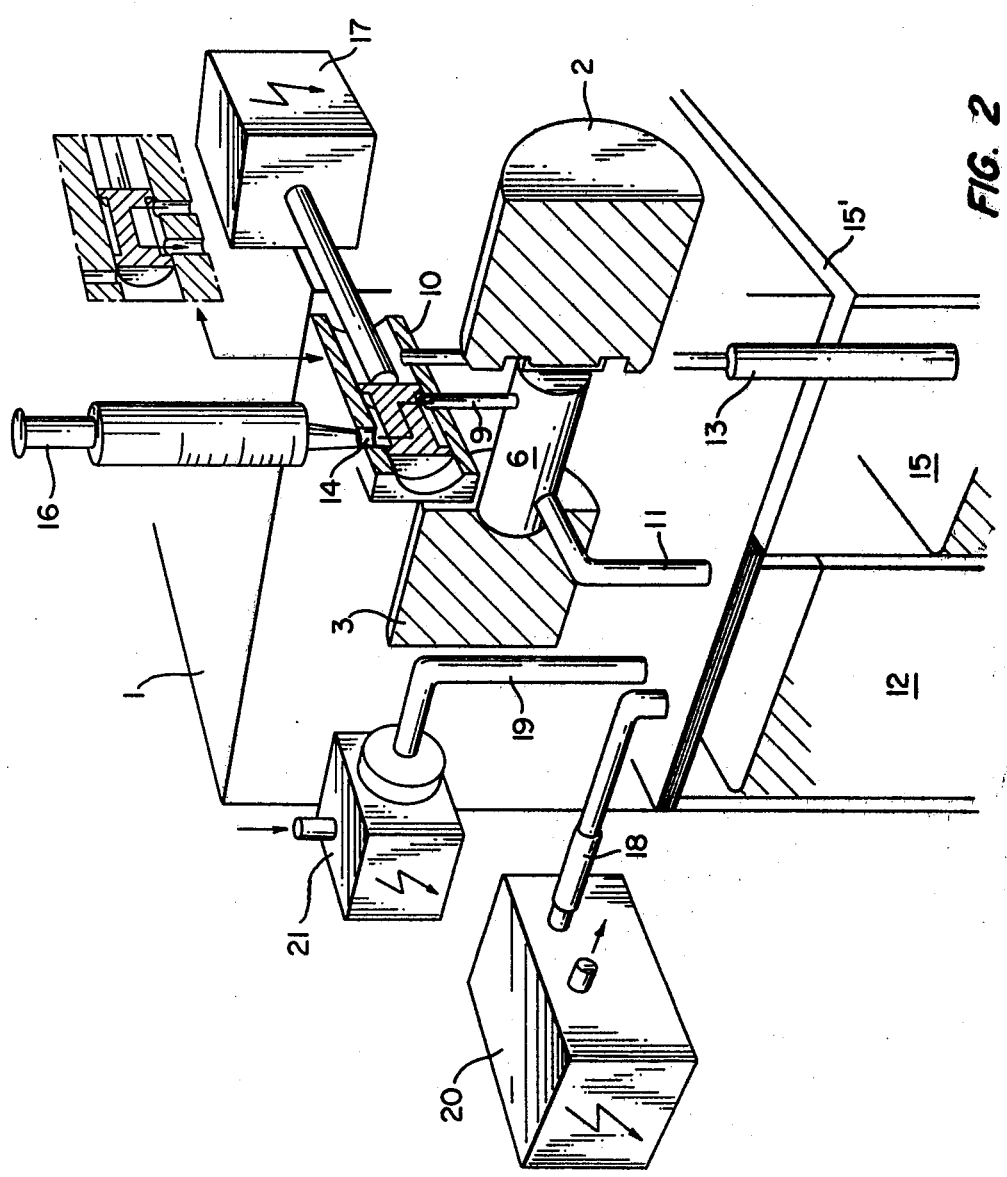
Figure 3:
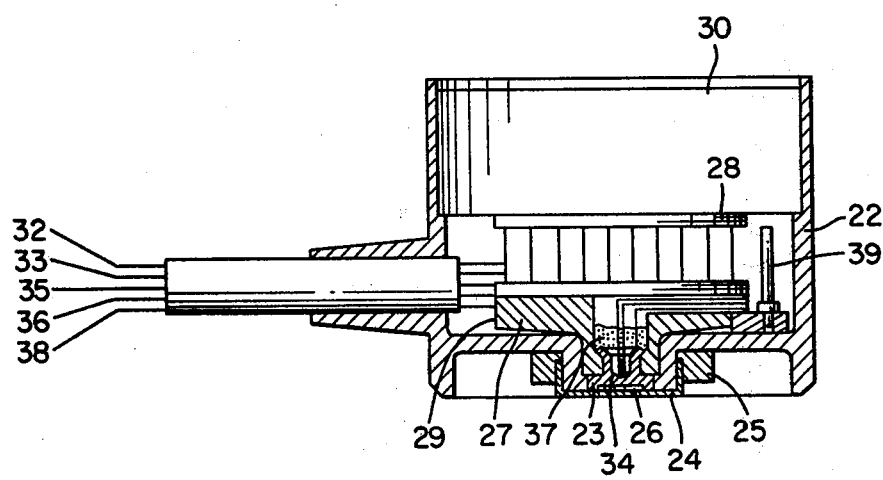
Figure 4:
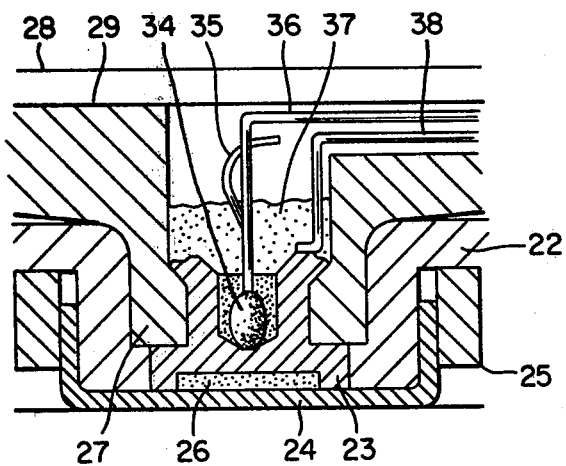
Figure 5:
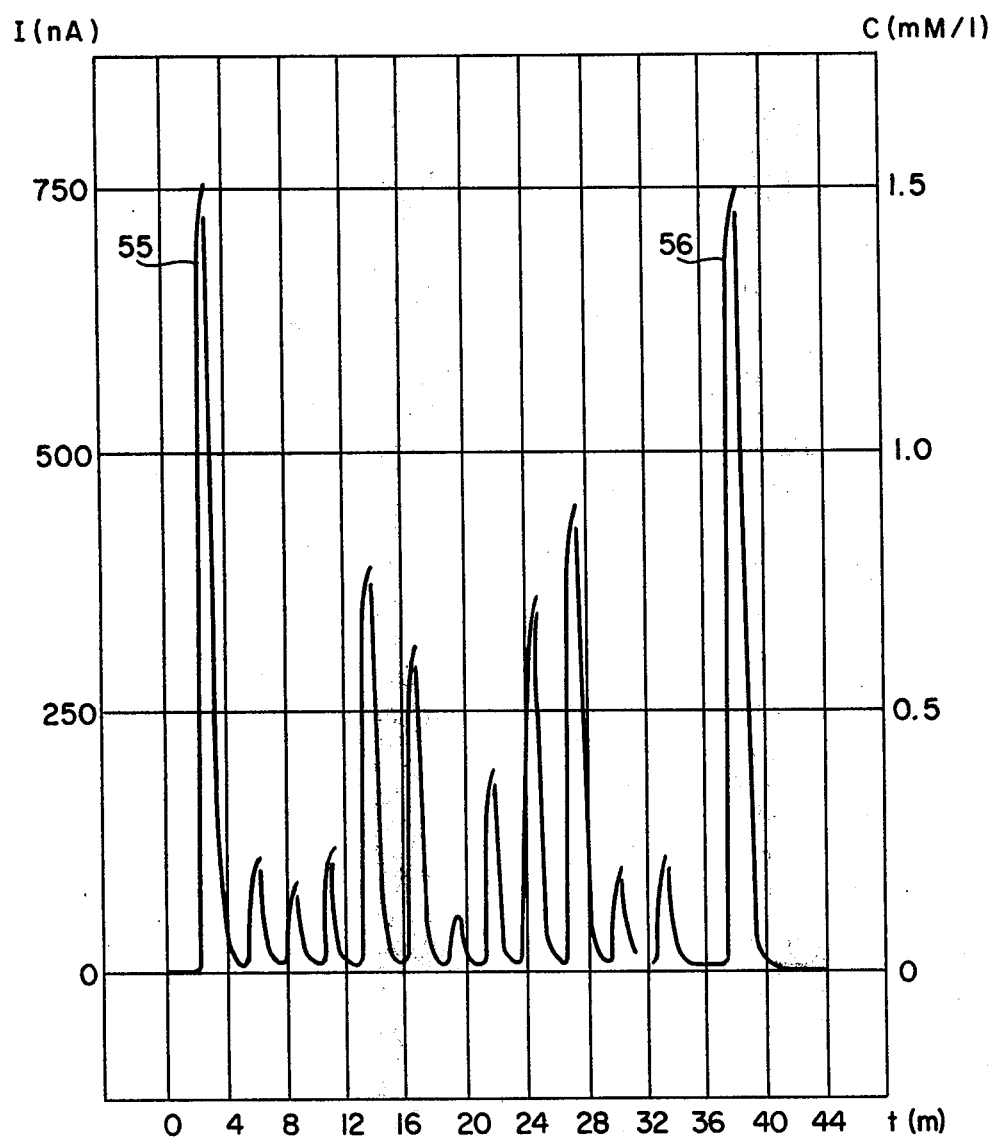

An embodiment of the invention will now be described with reference to the accompanying drawings, in which:

FIG. 1 is a schematic block diagram of an automatically-controlled device for determining the concentration of a substrate in a fluid sample, FIG. 2 is a perspective view of a preferred embodiment of the device, FIG. 3 is a cross-section of a temperature-controlled enzyme electrode, FIG. 4 shows a part of the cross-section shown in FIG. 3, and FIG. 5 is a typical graph of current vs. time during the measurement of the lactate concentration in diluted solutions of heparinised samples of human blood.

As FIGS. 1 and 2 shows, the device according to the invention comprises a measuring-cell system comprising a temperature-controlled enzyme electrode 2, a reference electrode 3 and a measuring cell 6 in the form of a very small tubular chamber for receiving the test solution and disposed between the contact surfaces 4, 5 of the electrodes. The measuring-cell system 1 comprises ducts 7, 8 (diagrammatically shown in FIG. 1), duct 7 connecting cell 6 via a line 9 to a distributor 10 mechanically coupled to the measuring-cell system and duct 8 connecting cell 6 via a line 11 to a container 12 for receiving waste solutions sucked from cell 6. System 1 and distributor 10 are partly made of transparent material. Two supply lines 13, 14 terminate in distributor 10. Line 13 connects the distributor to a container 15 which contains a buffer solution containing an acceptor and is always open to the exterior through an aperture 15'. Line 14 connects the distributor to a syringe 16 for introducing a fluid sample into the measuring cell. Distributor 10 can be controlled by an electromagnet 17 for providing a connection between line 13 or 14 and line 9. Container 12 is externally closed and connected by lines 18, 19 only to a vacuum pump 20 and to an air valve 21 respectively. The vacuum pump is used to provide a negative pressure in container 12 which, depending on the position of the distributor, causes buffer solution to flow from container 15 into measuring cell 6 or sucks waste solutions from cell 6 into container 12. The air valve is used to overcome the negative pressure produced in container 12 by the vacuum pump and thus interrupts the flow caused by the pressure difference. Pump 20 and valve 21 are electrically controlled. FIG. 3 shows a detail of the construction of the temperature-controlled enzyme electrode 2 disposed in the measuring-cell system. A holder (a cylindrical plastics block 22) has a cylindrical recess surrounded by an annular projection. A platinum or gold electrode 23 is disposed in the recess. The platinum or gold electrode also has a cylindrical recess approximately 0.2 mm deep. The edge of the projection and the outer annular surface of the platinum or gold electrode are on the same plane. A regenerated cellulose semi-permeable membrane 24 is secured by a retaining ring 25 disposed outside the projection. An enzyme-containing layer 26 is disposed between membrane 24 and the surface of the cylindrical recess in sensor 23. Sensor 23 is surrounded by a cylindrical projection of a disc-shaped aluminium component providing a thermal connection between the platinum or gold electrode and a Peltier cell 28 mounted on the aluminium component. The aluminium component is electrically insulated by an oxide layer 29 from all other components. The Peltier element is cooled by a cooling fin 30.

As FIG. 2 shows, the Peltier cell 28 is controlled by a temperature regulating unit 31 which maintains the temperature of the platinum or gold electrode at a constant predetermined value between 10° and 20° C. The temperature of the platinum or gold electrode 23 is regulated in order to regulate the temperature of the enzyme-containing layer 26 since, as already mentioned, the enzymatic reaction occurring in this layer is dependent on temperature. The aforementioned device can very rapidly and efficiently regulate the temperature of layer 26, since the thermal resistance between the Peltier cell and layer 26 is very low. A thermistor 34 is disposed in a bore in platinum or gold electrode 23 and thermally coupled thereto and connected to the temperature-regulating unit 31, so that the latter can form a signal representing the actual temperature of the platinum or gold electrode.

As FIG. 3 shows, an epoxy filling 37 is used to secure thermistor 34 in the bore in the platinum or gold electrode. Unit 31 is connected via lines 32, 33 to the Peltier cell 28 and via lines 35, 36 to the thermistor 34. Platinum or gold electrode 23 is connected via line 38 to a d.c.

source 40. All electric connections to the exterior are made via connecting terminals 39.

Depending on the substrate, the following enzymes are used in the enzyme electrode.

| Substrate | Enzyme |
|---|---|
| Glucose | Glucose-oxidase |
| Lactate | Cytochrome $b_2$ |

The criteria for selecting the properties of the enzyme and the memebrane will be explained hereinafter with reference to the measurement of the lactate concentration. In order to be used in a clinic or analytical laboratory, the enzyme electrode must satisfy the following conditions. Firstly, if a sufficient quantity of acceptor is present in the enzyme-containing layer 26, the permanent current flowing through the platinum or gold electrode 23 must be proportional to the lactate concentration in the test solution up to a concentration of approx. 15 mM/l. Secondly, in spite of the unavoidable reduction in enzyme activity during operation, the progressive deviation in the permanent current must be very low after the enzyme electrode has been calibrated. Thirdly, the response time of the enzyme electrode must be very short ($\leq$ 2 min). In order to satisfy these three conditions, it it preferable to use membranes having low permeability and short induction times (a measurement of the time required by a membrane to enable stationary diffusion of the substrate to occur through the membrane). Commercial cellophane membranes have a short induction time for lactate, but are highly permeable, so that very active enzyme solutions have to be used. If the most active cytochrome-$b_2$ solutions at present available are used (approx. 2000 U/ml at 25° C.), the progressive deviation in the measured values can be kept low for a few days after the enzyme electrode has been calibrated. If the enzyme electrode is to be manufactured economically, however, it should be usable without any maintenance for a number of weeks. This can be achieved by using low-permeability membranes or by diluting the fluid sample. Since no reliable low-permeability membranes are at present available the second method is chosen. It has been found that the most advantageous dilution ratio is 1:10, which reduces the measuring range to 0 to 1.5 mM/l. Dilution ratios between 1:5 and 1:20, however, may also be used. In the aforementioned enzyme electrode, PUDO/193 cellophane membranes manufactured by Du Pont and cytochrome-$b_2$ solutions having an activity of approx. 2000 U/ml are used. An enzyme electrode prepared in this manner can be used for at least a month for measuring the lactate concentration in dilute biological fluids in a range from 0 to 1.5 mM/l. The response time of the enzyme electrode is between 50 and 120 seconds if the temperature of the platinum or gold electrode is kept constant at 18° C.

The enzyme activity decreases progressively with time during operation, with a resulting reduction in the current produced by the enzymatic reaction and an increase in the response time of the enzyme electrode. The enzyme becomes unserviceable when the permanent current ceases to be proportional to the lactate concentration or when the response time of the enzymatic electrode becomes too long (more than 2 minutes).

Maintenance of the enzyme electrode is simple. When the enzyme becomes unserviceable, the old enzyme and the membrane are removed, the contact surface of the platinum or gold electrode is carefully cleaned and coated with a new enzyme solution and a new membrane is assembled. These maintenance operations can be performed by an experienced person in about 5 minutes, after which the enzyme electrode can be used for at least a month without further maintenance.

The reference electrode 3 shown in FIGS. 1 and 2 is e.g. a silver chloride electrode. The working life of the enzyme used in the enzyme electrode is shortened by the ions given off by the silver chloride electrode. Advantageously, in order to protect the enzyme from these ions, the reference electrode is covered with a glass frit (nor shown) or membrane preventing ions from flowing out of the reference electrode.

As FIG. 1 shows, the platinum or gold electrode of electrode 2 is directed to the reference electrode 3 via line 38, d.c. source 40, a current amplifier 41 and a line 42. In order to measure the current flowing through the resulting loop, the digital indicating ammeter 43 is connected to one output of the current amplifier 41. During each measurement of the concentration of substrate, a window discriminator 44 connected in parallel to the ammeter is used for rapidly determining the peak value of the current measured by the ammeter. When the current increases the window discriminator compares each two successively scanned measured values. If the difference between the two is smaller than a given reference value, the window discriminator gives signals which block the digital indicator of ammeter 43 indicating the measured peak value and actuate an indicator lamp 45 which warms the operator. If the entire indicating device is suitably calibrated by potentiometers 46, 47, the concentration of substrates in a fluid sample can be directly read off the digital scale of the ammmeter 43, which is calibrated in mM/l. The current amplifier 41 has an additional output 48 which gives a signal for recording purposes.

As FIG. 1 shows, a control unit 49 is provided for cyclic electric control of distributor 10, vacuum pump 20, air valve 21 and window discriminator 44. Two press buttons 50, 51 are provided for operating this unit. Button 50 starts a cleaning process wherein cell 6 is filled with buffer solution from container 15. Button 51 initiates a suction process wherein cell 6 and all the lines between the syringe input of the line 14 and the output of line 11 are completely emptied into container 12. At the end of this process, an indicator lamp 52 controlled by the control unit shows that the device is ready to receive a fluid sample.

In the aforementioned device, potassium hexacyanoferrate-(III) is used as the acceptor when measuring the concentration of lactate or glucose. Depending on the substrate, buffer solutions having the following concentrations of acceptor are used:

| Substrate | Concentration of Acceptor* (mM/l) |
|---|---|
| Lactate | 1 – 2 |
| Glucose | 10 |

*If the dilution ratio of the fluid sample is approx. 1:10.

The buffer solution used is a isotonic phosphate solution, pH = 7.2. The container 15 must be filled with fresh buffer solution every day. This maintenance operation can easily be performed by suitably disposing the container in the device.

Since a sufficient quantity of the acceptor must be added to the enzyme-containing layer before each measurement, the fluid sample does not need to contain an acceptor. If diluted biological fluids are used as the fluid sample, they can rapidly and accurately be diluted by means of commercialy available devices. With regard to the preparation of fluid sample, it is important to note that when the blood lactate concentration is measured, the erythrocytes in the blood sample cause the lactate concentration to increase during the time between the withdrawal of the blood sample and the introduction of the fluid sample into the measuring cell. In order to obtain an accurate measurement, this intermediate time must be reduced to a minimum.

The device is calibrated in the following manner. After a new enzyme electrode has been disposed in the measuring-cell system, the measuring cell is filled with the buffer solution. After a waiting time of 10 to 15 minutes during which the basic current reaches its permanent value, the potentiometer 46 is used for zero adjustement. Next, the buffer solution is sucked from the measuring cell and replaced by test solutions containing a known concentration of lactate. On each occasion, the current amplification is adjusted by potentiometer 47 so that the known concentration of lactate can be directly read off the digital indicator of the ammeter. Since the current flowing through the platinum or gold electrode is easily reproducible and deviates very slightly with time, the device needs to be calibrated only at intervals of several hours. In practice, it is often possible to use an enzyme electrode for several days without re-calibration. After each calibration or measurement, the fluid sample is withdrawn from the cell and replaced by the buffer solution.

Next, the acceptor in the buffer solution diffuses through the semi-permeable membrane of the enzyme electrode into the enzyme-containing layer. Meanwhile, the current flowing through the platinum or gold electrode falls in 2 or 3 minutes to the permanent value of the basic current and a new fluid sample can be introduced into the cell. In order to obtain maximum accuracy, the amounts of fluid sample used for calibration and measurement must be about the same.

The measuring cell, therefore, is filled with buffer solution before each measurement, so that the enzyme-containing layer receives a sufficient quantity of the acceptor and the basic current flowing through the platinum or gold electrode does not appreciably affect the measurement.

Using the aforementioned device, a measurement is performed as follows. The operator presses button 51, whereupon the control unit 49 controls distributor 10, vacuum pump 20 and air valve 21. Distributor 10 is actuated by electromagnet 17 and connects lines 9 and 13. Air valve 21 is closed and pump 20 is set in operation. The pump produces a negative pressure in container 12 so that the buffer solution is sucked from cell 6 into container 12. After a certain time, during which the measuring cell and the lines connected thereto are completely emptied, the pump is switched off, the valve is opened, the window discriminator 44 is switched on and the indicator lamp 52 shows that the device is ready to receive a fluid sample. Next, the test solution is introduced into cell 6 by a syringe through line 14, distributor 10 and lines 9 and 7. Thereupon, the current flowing through the platinum or gold electrode first increases rapidly, reaches a peak value after 50 to 120 seconds and then slowly decreases since the concentration of acceptor in the enzyme-containing layer becomes smaller owing to diffusion of the acceptor into the measuring cell. The initial increase in current can be observed by the digital indicator of ammeter 43. The relative increase in current is compared with a given reference value in the window discriminator. The peak value of the current is reached when the relative increase is smaller than the given reference value. As soon as the saturation value of the current has been measured, discriminator 44 supplies a signal blocking the digital indicator of ammeter 43, so that the substrate concentration can be read off. Simultaneously discriminator 44 switches on the indicator lamp 45, so that the operator notices the displayed concentration value. After the operator has read off the displayed value, he presses button 50, whereupon the control unit 49 controls distributor 10, pump 20 and valve 21 and inactivates discriminator 44, so that the digital indicator is no longer blocked. Lines 9 and 13 are connected by the distributor, the air valve is closed and the vacuum pump is started. Thereupon, owing to the negative pressure produced by the vacuum pump in container 12, the test solution is sucked from cell 6 into container 12 and the buffer solution flows from container 15 into cell 6. After a given time, i.e., after the measuring cell and the lines connected thereto are filled with buffer solution, the pump is switched off and the air valve is opened. After 2 to 3 minutes, the current flowing through the platinum or gold electrode again falls to the permanent value of the basic current and a new measurement can be started.

As shown by the current graph in FIG. 5, the calibration curves 55, 56, respectively made before and after a series of measurements are practically identical although the enzyme electrode had already been 28 days in service at the time of the experiment. These results show that measurements made by the enzyme electrode according to the invention are extremely stable and reproducible.

The main advantages of the method according to the invention are the following: Firstly, the required temperature regulation is quicker and extremely efficient, as the volume of temperature-regulated fluid is reduced to the volume of the enzyme-containing layer. Secondly the acceptor does not have to be added to each fluid sample (this reduces the amount of labour required). Thirdly, the peak value of the current flowing through the platinum or gold electrode is measured by an electronic circuit, thus greatly shortening the time required for each measurement.

The device according to the invention also has the following advantages. Since all the measuring operations are automatic, apart from the introduction of fluid sample into the cell, and since a window discriminator is used, the measurements can be made much more quickly (up to approx. 20 measurements per hour) than in previously-used devices. The device is very easy to operate and maintain, both of which can be performed by assistants. Since the measuring cell is very small, the measurements can be made on correspondingly small volumes of fluid sample (approx. 100 ul.) We can also assume that, if a device of the aforementioned kind is present, a wider range of measurements can be made on various substrates of enzyme reactions for diagnostic purposes. For example, the blood lactate concentration in new-born infants can be measured at intervals of a few minutes, which is impossible using existing methods and devices.

The enzyme electrode according to the invention has two basic advantages. Firstly, the temperature of the enzyme-container layer can be very rapidly and efficiently regulated, since the thermal resistance between the Peltier cell and the enzyme-containing layer is very small. Secondly since the Peltier cell and the thermistor are incorporated in the enzyme electrode, the dimensions of the measuring cell in the measuring device are very small and the amount of fluid sample required per measurement can in that way be reduced to a minimum of approx. 100 µl.

We claim:

1. A method of measuring the concentration of substrates of enzyme reactions occurring during intermediate metabolism, more particularly the concentration of lactate and glucose in fluid biological samples, wherein the substrate concentration is measured by measuring a current produced by oxidation of an acceptor at an enzyme electrode with a measuring device substantially comprising a measuring cell for receiving the fluid sample, the enzyme electrode and a reference electrode, both electrodes being in contact with the fluid sample, and the enzyme electrode containing a platinum or gold electrode, an enzyme layer and a semi-permeable membrane covering the enzyme layer, the temperature at which the enzymatic reaction takes place being regulated at a pre-determined value and a direct voltage being applied between the enzyme electrode and the reference electrode, which method is characterized by performing a local temperature regulation of the enzyme layer within the enzyme electrode by means of a temperature control of the gold or platinum electrode thereof, filling the measuring cell with a buffer solution containing an acceptor prior to filling the cell with a fluid sample and keeping the cell filled with said buffer solution over a time interval long enough to enable diffusion of a quantity of the acceptor through the semi-permeable membrane of the enzyme electrode into the enzyme-containing layer, said quantity of acceptor being sufficiently high for assuring a linear response of the enzyme electrode, sucking the buffer solution from the measuring cell at the end of said time interval, filling the measuring cell with a fluid sample and measuring the concentration of the substrate contained in the fluid sample by determining the peak value of the current flowing through the enzyme electrode with an electronic circuit.

2. A method according to claim 1, wherein potassium hexacyanoferrate-(III) is used as an acceptor for measuring the concentration of glucose in fluid biological samples.

3. A method according to claim 2, wherein the fluid samples are diluted biological fluids.

4. A method according to claim 3, wherein the dilution ratio is between 1:5 and 1:20.

* * * * *